(12) United States Patent
Faure et al.

(10) Patent No.: US 9,884,033 B2
(45) Date of Patent: *Feb. 6, 2018

(54) AMINO ACID SUPPLEMENTATION FOR A HEALTHY MICROBIOTA ECOSYSTEM

(71) Applicant: NESTEC S.A., Vevey (CH)

(72) Inventors: Magali Faure, Mollie-Margot (CH); Florence Rochat, Montreux (CH); Denis Breuille, Epalinges (CH); Irene Corthesy Theulaz, Epalinges (CH)

(73) Assignee: Nestec S.A., Vevey (CH)

( * ) Notice: Subject to any disclaimer, the term of this patent is extended or adjusted under 35 U.S.C. 154(b) by 1 day.

This patent is subject to a terminal disclaimer.

(21) Appl. No.: 14/995,847

(22) Filed: Jan. 14, 2016

(65) Prior Publication Data

US 2016/0128960 A1    May 12, 2016

Related U.S. Application Data

(60) Continuation of application No. 14/338,583, filed on Jul. 23, 2014, now Pat. No. 9,271,958, which is a continuation of application No. 12/135,868, filed on Jun. 9, 2008, now abandoned, which is a division of application No. 10/564,807, filed as application No. PCT/EP2004/064269 on Jun. 16, 2014, now abandoned.

(30) Foreign Application Priority Data

Jun. 23, 2003 (EP) .................... 03014037

(51) Int. Cl.
| | | |
|---|---|---|
| A61K 31/195 | (2006.01) | |
| A61K 31/198 | (2006.01) | |
| A61K 31/401 | (2006.01) | |
| A23K 20/147 | (2016.01) | |
| A23K 20/142 | (2016.01) | |
| A23K 50/40 | (2016.01) | |
| A61K 9/00 | (2006.01) | |
| A23L 33/00 | (2016.01) | |
| A23L 33/175 | (2016.01) | |

(52) U.S. Cl.
CPC .......... *A61K 31/198* (2013.01); *A23K 20/142* (2016.05); *A23K 20/147* (2016.05); *A23K 50/40* (2016.05); *A23L 33/175* (2016.08); *A23L 33/40* (2016.08); *A61K 9/0095* (2013.01); *A61K 31/195* (2013.01); *A61K 31/401* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,491,589 A | 1/1985 | Dell et al. |
| 4,886,747 A | 12/1989 | Derynck et al. |
| 5,310,768 A | 5/1994 | Vinnars |
| 5,322,836 A | 6/1994 | Seiichi et al. |
| 5,411,757 A | 5/1995 | Buist et al. |
| 5,444,054 A | 8/1995 | Garleb et al. |
| 5,531,988 A | 7/1996 | Stephen |
| 5,658,895 A | 8/1997 | Aoi et al. |
| 5,756,481 A | 5/1998 | Arnal et al. |
| 5,863,906 A | 1/1999 | Arnal et al. |
| 6,166,181 A | 12/2000 | Jacobson et al. |
| 6,180,991 B1 | 1/2001 | Yamazaki |
| 6,183,099 B1 | 1/2001 | Stephen |
| 6,833,350 B2 | 12/2004 | Bellevre et al. |
| 6,849,593 B1 | 2/2005 | Forssmann et al. |
| 7,468,193 B2 | 12/2008 | Schiffrin et al. |
| 9,271,958 B2 * | 3/2016 | Faure ............. A23L 33/175 |
| 2001/0031723 A1 | 10/2001 | Ballevre et al. |
| 2001/0033856 A1 | 10/2001 | Zohoungbogbo |
| 2003/0008016 A1 | 1/2003 | Albert |
| 2003/0054083 A1 | 3/2003 | Gohman et al. |
| 2003/0064104 A1 | 4/2003 | Stillman |

FOREIGN PATENT DOCUMENTS

| | | |
|---|---|---|
| CA | 2404005 | 10/2001 |
| CN | 1181244 | 5/1998 |
| DE | 10024746 | 11/2001 |
| EP | 1228707 | 8/2002 |
| EP | 1281325 | 2/2003 |

(Continued)

OTHER PUBLICATIONS

Bruck et al., "Use of batch culture and a two-stage continuous culture system to study the effect of supplemental alactalbumin and glycomacropeptide on mixed populations of human gut bacteria", FEMS Microbiology Ecology, Jul. 5, 2002, pp. 231-237.

(Continued)

*Primary Examiner* — Karlheinz R. Skowronek
*Assistant Examiner* — Ronald T Niebauer
(74) *Attorney, Agent, or Firm* — K&L Gates LLP

(57) ABSTRACT

A nutritional composition is used to reconstitute an optimal healthy microbiota ecosystem in humans or animals. In particular, an ingestible carrier contains specific amino acids designed to favor the growth of bacteria favorable to individuals health or for reducing the risk of developing deleterious events. In another aspect, specific amino acids are used to reconstitute an optimal healthy microbiota ecosystem in humans or animals, in particular in infants, critically ill patients, in the case of chronic diseases or any stresses impacting the gut and in elderly people.

6 Claims, 1 Drawing Sheet

(56) References Cited

FOREIGN PATENT DOCUMENTS

| GB | 1159615 | 7/1969 |
|---|---|---|
| WO | 9913738 | 3/1999 |
| WO | WO9914231 | 3/1999 |
| WO | WO0022945 | 4/2000 |
| WO | WO0156405 | 8/2001 |
| WO | WO0158283 | 8/2001 |
| WO | WO0160346 | 8/2001 |
| WO | WO0178533 | 10/2001 |
| WO | WO0215719 | 2/2002 |

OTHER PUBLICATIONS

Le Floc'H et al.,"Le devenir des proteines et des acides amines dans l'intestin du porc: de la digestion a l'apparition dans la veine porte", INRA Prod. Anim. 2000, pp. 303-314, vol. 13, No. 5.

Heavey et al., "The Gut Microflora of the Developing Infant: Microbiology and Metabolism", Microbial Ecology in Health and Disease, 1999, pp. 75-83.

Lonnerdal, "Nutritional and physiologic significance of human milk proteins", Am. J. Nutr., 2003, pp. 1537S-1543S, vol. 77.

Marshall, "Casein Macropeptide From Whey—A New Product Opportunity", Food Research Quarterly, 1991, pp. 86-91.

Myrie et al., "Diets that increase mucin production in pigs reduce threonine and amino acid retention", Advances in Pork Production, 2003, vol. 14, Abstract No. 9.

Posati et al., "Composition of Foods", Agriculture Handbook No. 8-1, Nov. 1976.

Souci et al., "Food Composition and Nutrition Tables", 2008.

Shahjee et al., J. Biosci., vol. 27 (2002), pp. 515-520.

Clark et al., http://www.hortnet.co.nz/publications/science/smart.htm (accessed Feb. 2008) originally published in NZ Kiwifruit Dec. 1994, 4 pgs.

Taras DCB ("The desired ideal: healthy gut and microbiota stability" Lohmann information vol. 44(1) Apr. 2009 pp. 30-38 retreived from http://www.lohmann-information.com/content!1_i_44_artike14.pdf on Aug. 6, 2012).

Chemistry web site retrieved from http://wps.prenhall.com/wps/media/objects/3311/3390593/b1b0508.html on Aug. 6, 2012, 7 pages.

Droge et al ('Role of cysteine and glutathione in HIV infection and other diseases associated with muscle wasting and immunolgogical dysfunction' the FASEB Journal v11 Nov. 1997 pp. 1077-1089).

NMSEA web site entry for 'What are the different forms of energy?' retrieved from http://www.nmsea.org/Curriculum/Primer/forms_of_energy.htm on Apr. 16, 2012 4 pages.

Puntis et al ('Egg and breast milk based nitrogen sources compared' Archives of Disease in Childhood 1989 v64 pp. 1472-1477).

Mitton (Journal of Pediatric Gastroenterology and Nutrition 'Review:Amino acids and lipid in total patenteral nutrition for the newborn' v18 (1994) pp. 25-31).

Escarabajal et al (Alcohol 'L-cysteine, a thiol amino acid, increases the stimulating acute effect of ethanol on locomotion'v25 (2001) pp. 83-88).

Neutra, M.R., "Gastrointestinal mucus: synthesis, secretion, and function." Physiology of the gastrointestinal tract (1987): pp. 975-1009.

Sonnenburg et al. "Getting a grip on things: how do communities of bacterial symbionts become established in our intestine?" Nature Immunology, vol. 5, No. 6, pp. 569-573.

Corfield et al. "Mucins and mucosal protection in the gastrointestinal tract: new prospects for mucins in the pathology of gastrointestinal disease" Gut, vol. 47, 2000, pp. 589-594.

NIH MedicinePlus (retrieved from http://www.nlm.nih.gov/medlineplus/magazines/issues/spring11/articles/spring11pg24-25.html on May 11, 2015, 2 pages.

Sasaki et al. ('The role of bacteria in the pathogenesis of ulcerative colitis' Journal of Signal Transduction 2012 ID704953 pp. 1-6).

Scaldaferri et al ('The gut barrier new acquisitions and therapeutic approches' J Clin Gastroenterol v46 2012 pp. s12-s17).

ACAAI (retrieved from http://acaai.org/allergies/types on May 11, 2015, 6 pages).

Thomas et al ('Dietary intake and nutritional treatment in childhood Crohn's disease' Journal of pediatric gastroeneterology and nutrition v17 1993 pp. 75-81).

Corfield et al ('Colonic mucins in ulcerative colitis: evidence for loss of sulfation' Glycoconjugate Journal v13 1996 pp. 809-822).

Raouf et al ('Enterl feeding as sole treatment for Crohn's disease: controlled trial of whole protein v amino acid based feed and a case study of dietary challenge' Gut v32 1991 pp. 702-707).

* cited by examiner

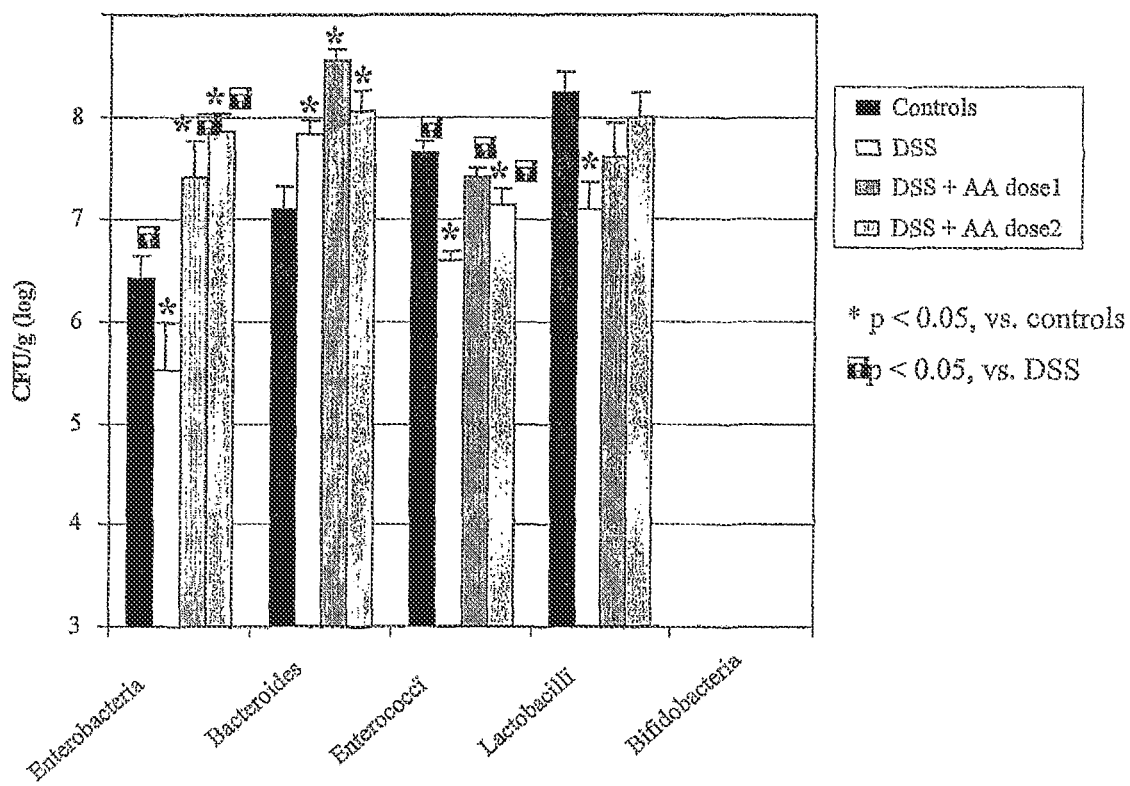

AMINO ACID SUPPLEMENTATION FOR A HEALTHY MICROBIOTA ECOSYSTEM

PRIORITY CLAIM

This application is a continuation of U.S. patent application Ser. No. 14/338,583 filed Jul. 23, 2014, which is a continuation of U.S. patent application Ser. No. 12/135,868 filed Jun. 9, 2008, which is a divisional of U.S. patent application Ser. No. 10/564,807 filed May 17, 2006, which is a National Stage of International Application No. PCT/EP2004/064269 filed Jun. 16, 2004, which claims priority to European Application No. 03014037.0 filed Jun. 23, 2003, the entire contents of which are incorporated herein by reference.

FIELD OF THE INVENTION

The present invention pertains to a nutritional composition for reconstituting an optimal healthy microbiota ecosystem in humans or animals. In particular, the present invention relates to an ingestible carrier containing specific amino acids designed to favor the growth of bacteria favorable to individuals health or for reducing the risk of developing deleterious events. The invention also pertains to the use of specific amino acids for reconstituting an optimal healthy microbiota ecosystem in humans or animals, in particular in infants, critically ill patients, in the case of chronic diseases or any stresses impacting the gut and in elderly people.

BACKGROUND OF THE INVENTION

The gastrointestinal microbiota has been shown to play a number of vital roles in maintaining gastrointestinal tract functions and overall physiological health, playing a role in the control of bacterial overgrowth, bacterial translocation, nutrient availability, immune stimulation, septicemia as well as pathogenic development. The microbiota closely interacts with many components of the gut and is one primary actor involved in the gut barrier function. It also participates in the protection of individuals from pathogens attack by adequately stimulating the immune system and interfering with pathogens virulence. For all those reasons, a well balanced microbiota is a guarantee for the maintenance of a healthy gut and intestinal barrier function.

The intestinal tract is colonized by microorganisms, such as Bacteroides, Lactobacilli, Bifidobacteria and also *E. coli*. The maintenance of a normal colonization of the gut by those specific strains (quantitative and qualitative) is essential in insuring a healthy gastrointestinal tract protection and function.

However, this important but vulnerable balance of the gastrointestinal ecosystem can be altered by many factors such as antibiotic treatment, drug, change in diet, environmental factors such as psychological or physiological stress, age, surgery, and pathologic conditions (IBD) within the gastrointestinal tract and pathologic conditions.

An impaired balance of the ecosystem may result in impairing the gut barrier function, by reducing its protective action against pathogens attack and virulence and its beneficial stimulating action on individual's immune system. Such alterations will impair the gut barrier integrity and function and may result in increased bacterial translocation and allergy risks.

In the art several means have already been proposed to impact the bacterial balance of the gut. For example, CN 1181244 provides a health care oral liquid prepared through acclimating, culturing and amplifying thermophilic lactostreptococcus and acidophilic lactobacillus in defatted milk containing bone slurry. This liquid rich in activated calcium, vitamins and amino acids is used to regulate bacterial balance in the intestine.

Also, in BE 694500, a dietetic alimentary product having adequate and non-residual nutritivity is designed for reducing the intestinal flora, consists of an aqueous emulsion of a water-soluble constituent (II), a fat-soluble constituent (III) and an emulsifier; (II) being an aqueous solution of water-soluble vitamins, mineral salts, carbohydrates and a nitrogen source chosen from amino acids, amino acid derivatives, protein hydrolysates and mixtures thereof; and (III) being fat-soluble vitamins and a material chosen from molecularly defined fats, substitutes for molecularly defined fats and fatty acids. This composition gives rise to a reduction in blood-ammonia levels and a reduction in hypertension caused by toxic metabolites (e.g. tyramine) of intestinal bacteria. Other benefits of a reduced intestinal microflora include the lower doses of antibiotics required for the treatment of infections.

However, there is still a need for a nutritional composition that is capable of promoting a well-balanced intestinal microbiota. Therefore, an object of the present invention is to provide improved means to promote the growth of the gut microbiota and to promote or restore an optimal intestinal microbiota ecosystem in an individual beneficial for it.

SUMMARY

During the studies leading to the present invention the present inventors have realized that the above object may be solved by providing a specific amino acids supplementation to the individual.

In fact, it has been found that by supplementing the diet of the individual with specific amino acids, microbiota growth may be selectively stimulated. It can also modulate the equilibrium of the microbiota and restore healthy balance microflora.

Consequently, in a first aspect the present invention provides a nutritional composition for promoting an optimal microbiota ecosystem in humans or animals, which comprises at least an amino acid being selected in the group consisting of hydroxyl amino acids, sulfur-containing amino acids or heterocyclic amino acids or their derivatives and added in an amount efficient to favor a healthy equilibrium of the gut microbiota.

In a second aspect, the invention provides use of at least one amino acid being added over the normal nutritional needs, for the preparation of a food composition or medicament for favoring the growth of bacterial microbiota and promoting an optimal balance of gut ecosystem, which is favorable to individuals health and thus reducing the risk of developing deleterious events.

In a third aspect, the invention provides use of at least one amino acid according to an embodiment of the invention for the preparation of a food composition or medicament for reinforcing intestinal barrier and immune defenses.

In a fourth aspect, the invention provides use of at least one amino acid according to an embodiment of the invention for the preparation of a food composition or medicament for reducing risks of allergy, in particular in infants.

In a last aspect the invention provides methods of promoting an optimal balance microbiota, modulating qualitatively and quantitatively the microbiota, reinforcing intestinal barrier and immune defenses, or reducing risks of allergy which comprise administering an effective amount of at least one amino acid according to an embodiment of the invention.

The composition according to the present invention, is particularly designed for critically ill patients, in the case of chronic diseases impacting the gut and in elderly people, infants or pets that present fragile ecosystem, to restore or maintain the integrity of their gut barrier. In fact, by reinforcing the equilibrium of the microbiota, it reinforces the intestinal barrier by interfering with pathogen virulence (competition with pathogens for adhesion sites, aggregation of pathogens, counteracting pathogen virulence).

Another advantage of the present invention is that it provides a specific amino acid composition modulating the equilibrium of the microbiota, which is disturbed in case of psychological, physiological, or environmental stress and therefore restores a healthy microbiota profile.

BRIEF DESCRIPTION OF THE FIGURE

FIG. 1 shows the effect of amino acid supplementation on count of rat's fecal Enterobacteria, Bacteroides, Enterococci, Lactobacilli and Bifidobacteria expressed in cfu/g (log).

DETAILED DESCRIPTION OF THE INVENTION

In the following description, the term microbiota means all the bacterial populations present in the digestive tract of the individual. Also, the term "supplementation" means that the amino acids are given in a proportion greater than the proportion corresponding to the requirement of a healthy man (for threonine which is an indispensable amino acid) or greater than the proportion corresponding to proteins usually used in products for non indispensable amino acids such as cysteine, serine and proline. Proteins usually used are for example milk proteins in product intended for human and vegetables and meat proteins for products intended for pets.

According to a first aspect, the composition according to the invention is supplemented with at least one amino acids selected in the group consisting of hydroxyl amino acids, sulfur-containing amino acids or heterocyclic amino acids. In a preferred embodiment, the amino acid is threonine, serine, cystein or proline or their derivatives, for example.

The amount of the amino acids to be used in the composition will vary depending upon factors such as the individual's condition, weight, the age, and whether the composition is the sole source of nutrition. However, as a source of hydroxyl amino acids, threonine may be added in an amount which implies a threonine intake in the range of 0.04 to 0.20 g/kg body weight/day, for example. In the same way, Serine may be added in an amount which imply a serine intake in the range of 0.07 to 0.35 g/kg body weight/day; sulfur-containing amino acids such as Cysteine may be added in an amount which imply a cysteine intake in the range of 0.03 to 0.15 g/kg body weight/day; and heterocyclic amino acids such as proline can be added in an amount which imply a proline intake in the range of 0.07 to 0.3 g/kg body weight/day, for example.

Those specific amino acids may be in the form of free amino acids or amino acids hydrolysates of different source of animal or plant proteins. They can be derived from a protein source enriched in those amino acids, for example whey proteins. The protein source may be in the form of intact proteins, hydrolyzed or partially hydrolyzed proteins or a mixture of intact and hydrolyzed proteins leading to peptides of different size. The protein source may also be enriched in form of synthetic peptides. It may also be enriched with free amino acids or entire proteins from natural source or synthetically peptides, or combinations thereof.

Such amino acids are conveniently administered in form of a product acceptable to the consumer, such as an ingestable carrier or support, respectively. Examples for such carriers or supports are a pharmaceutical, galenic or a food composition. Non-limiting examples for such compositions are milk, yogurt, curd, cheese, fermented milks, milk based fermented products, ice-creams, fermented cereal based products, milk based powders, infant formula, pet food, tablets, liquid bacterial suspensions, dried oral supplement, wet oral supplement, dry or wet tube feeding.

Accordingly, in a preferred embodiment, the invention provides a human food product that may be in the form of a nutritional formula, an infant formula, milk-based products, dairy products, cereal-based products, for example. To prepare such a food product or composition, the amino acid supplementation as described above can be incorporated into a food, such as cereal powder, milk powder, a yogurt, during its manufacture, for example.

If a nutritional formula is prepared, it may comprise, apart from the amino acid supplementation as mentioned above, a source of protein, a source of fat and a source of carbohydrate. Dietary proteins are preferably used as a source of protein. The dietary proteins may be any suitable dietary protein; for example animal proteins (such as milk proteins, meat proteins and egg proteins), vegetable or plant proteins (such as soy, wheat, rice or pea proteins. Milk proteins such as casein, whey proteins and soy proteins are particularly preferred. The composition may also contain a source of carbohydrates and a source of fat. The fat source preferably provides about 5% to about 55% of the energy of the nutritional formula. The lipids making up the fat source may be any suitable fat or fat mixture. Vegetable fats are particularly suitable; for example soy oil, palm oil, coconut oil, safflower oil, sunflower oil, corn oil, canola oil, lecithins, and the like. Animal fats such as milk fats may also be added if desired. The carbohydrate source preferably provides about 40% to about 80% of the energy of the nutritional formula. Any suitable carbohydrates may be used, for example sucrose, lactose, glucose, fructose, corn syrup solids, and maltodextrins, and mixtures thereof. Dietary fiber may also be added if desired. Numerous types of non-digestible dietary fiber are available. Suitable sources of dietary fiber, among others, may include soy, pea, oat, pectin, guar gum, and gum Arabic. If used, the dietary fiber preferably comprises up to about 5% of the energy of the nutritional formula. Suitable vitamins and minerals may be included in the nutritional formula in the usual manner to meet the appropriate guidelines. One or more food grade emulsifiers may be incorporated into the nutritional formula if desired; for example diacetyl tartaric acid esters of mono-diglycerides, lecithin and mono- and di-glycerides. Similarly suitable salts and stabilisers may be included.

The nutritional formula is preferably enterally administrable; for example in the form of a powder, a liquid concentrate, or a ready-to-drink beverage.

The nutritional formula may be prepared in any suitable manner. For example, the nutritional formula may be prepared by blending together the source of dietary protein, the carbohydrate source, and the fat source in appropriate proportions and the supplementation in amino acids according to the invention. If used, the emulsifiers may be included in the blend. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenized; for example in two stages.

If it is desired to produce a powdered nutritional formula, the homogenized mixture is transferred to a suitable drying apparatus such as a spray drier or freeze drier and converted to powder. The powder should have moisture content of less than about 5% by weight.

If it is desired to produce a liquid formula, the homogenized mixture is preferably aseptically filled into suitable containers as known in the art.

In another embodiment, a usual food product may be enriched with the specific amino acids according to the present invention. For example, a fermented milk, yogurt, a fresh cheese, a renneted milk, a confectionery bar, breakfast cereal flakes or bars, drinks, milk powders, soy-based products, non-milk fermented products or nutritional supplements for clinical nutrition.

In a further embodiment, a nutritionally complete pet food composition can be prepared. It may be in powdered, dried form, semi-moist or a wet, chilled or shelf stable pet food product. It can also be dietary supplements for pets or pharmaceutical compositions. These pet foods may be produced as is conventional. The amount of the pet food to be consumed by the pet to obtain a beneficial effect will depend upon the size of the pet, the type of pet, and age of the pet. However an amount of the pet food to provide a daily amount of about 0.9 g Threonine per 100 g dry matter would usually be adequate, for example.

An experiment showing that such a nutritional composition restores the gut microbiota ecosystem is presented in example 1. The properties of said amino acids have then been assessed by simple experiments, which show their impact on the intestinal microbiota. The amino acid supplementation and the above products may consequently be utilized for stimulating the growth of microbiota, modulating the microbiota and restoring a healthy balance microbiota ecosystem in the gut. It is also used to reinforce the intestinal barrier and stimulate the immune defenses. Thus, it helps to support the well being of individuals and/or the treatment and/or the prophylaxis of diseases.

The following non-limiting examples further illustrate the invention.

EXAMPLE 1

Effect of Specific Amino Acid Supplementation on the Intestinal Microbiota

In order to test the impact of specific amino acids towards the intestinal microbiota integrity, an in vivo experiment has been set up, wherein mixtures of four different amino acids were added as supplements in the normal diet of rats exhibiting an altered intestinal microbiota.

Material and Methods

An imbalance in the intestinal microbiota was obtained using an animal model (DSS-treated rats) exhibiting common clinical and histopathological features with the human ulcerative colitis pathology (Gaudio et al., 1999).

The animal experiment was conducted as follows: Male Sprague-Dawley rats (n=32) aged 10 months were randomly distributed into 4 experimental groups (described below). During an 8 days acclimatization period, rats had free access to tap water and received a control diet or diets supplemented in amino acids as described below. After this adaptation period, Dextran Sulfate Sodium (DSS)-treated rats received 5% DSS (w/v) in their drinking water for the first 9 days of the experiment and 2% DSS for the following 18 days to induce a chronic colitis.

Groups and diets were as follows:

i) Group "control": rats were fed ad libitum with a fish-based control diet (12% fish-based proteins, 8.2% fat). The control diet was balanced to meet all rat amino acid (AA) requirements. Its threonine, cysteine, proline and serine content were the following: Threonine: 5.7 g/kg of diet dry matter; Cysteine: 1.2 g/kg of diet dry matter; Proline: 4.8 g/kg of diet dry matter and Serine: 4.7 g/kg diet dry matter.

ii) Group "DSS": rats were fed ad libitum with the control diet. They received DSS (free access) dissolved in their drinking water as previously described.

iii) Group "DSS +AA dose1": rats were fed ad libitum with the control diet supplemented in Threonine (1.8-fold the normal requirements, supplementation with 5 g threonine/Kg diet dry matter), Cysteine (1.7-fold the normal requirements, supplementation with 4 g cysteine/Kg diet dry matter), Proline (1.9-fold the normal composition of the diet, supplementation with 5 g proline/Kg diet dry matter) and Serine (1.9-fold the normal composition of the diet, supplementation with 5 g serine/Kg diet dry matter).

iv) Group "DSS+AA dose2": rats were fed ad libitum with the control diet supplemented in Threonine (3.6-fold the normal requirements, supplementation with 15 g threonine/Kg diet dry matter), Cysteine (2.8-fold the normal requirements, supplementation with 7.2 g cysteine/Kg diet dry matter), Proline (3.9-fold the normal composition of the diet, supplementation with 15 g proline/Kg diet dry matter) and Serine (2.9-fold the normal composition of the diet, supplementation with 10 g serine/Kg diet dry matter).

All groups of rats received isonitrogenous diets.

At the end of the experiment, fecal samples were collected from animals with a sterile spoon into sterile tubes, frozen (liquid nitrogen) in 10% glycerol and then stored at −80° C. until analysis. The fecal microbiota was analyzed quantitatively for Enterobacteria, Bacteroides, Enterococci, Lactobacilli and Bifidobacteria species according to standard methods. Bacteria were counted using selective or semi-selective media. The counts were expressed as log (base 10) cfu/g feces with a lower detection limit of 3.30 log cfu/g and 5.50 log cfu/g of feces for Bacteroides.

Data are expressed as mean±SEM. One-way analysis of variance and Duncan's Multiple-Comparison Test were used to determine differences in gut microbiota among the groups. A difference was considered significant at $p<0.05$.

It will be appreciated that the skilled person may well examine other amino acids for their aptitude to impact the bacterial microbiota, by subjecting them to the conditions as detailed above or others.

Results

As shown in FIG. 1, the fecal microbiota was altered by the DSS treatment. Indeed, the Enterobacteria, Enterococci and Lactobacilli counts were significantly decreased in DSS-treated rats compared to controls while the Bacteroides counts were increased.

The amino acid supplementation exhibited significant effects on the count of several bacterial species. Part of the intestinal microbiota affected by the DSS treatment is restored with an amino acid supplementation. This study suggests that a supplementation in these specific amino acids may be beneficial for sick individuals, for example in the case of chronic or acute inflammation. This can be an advantage for improvement of clinical nutrition products.

EXAMPLE 2

Nutritional Formula

A nutritional composition for adult is prepared, and which contains for 100 g of powder: 15% of protein hydrolysate, 25% of fats, 55% carbohydrates (including maltodextrin 37%, starch 6%, sucrose 12%), traces of vitamins and oligoelements to meet daily requirements, 2% minerals and 3% moisture and 0.75 g Threonine, 1.35 g Serine, 1.2 g Proline and 0.45 g Cysteine.

13 g of this powder is mixed in 100 ml of water. The obtained formula is particularly intended for restoring or promoting intestinal microbiota in adults.

EXAMPLE 3

Nutritional Formula

A nutritional composition for critically ill patients, in the case of chronic diseases impacting the gut and in elderly people that present fragile ecosystem, is prepared as in example 1, but with a higher supplementation in the different amino acids. For 100 g of powder, this nutritional composition contains 1.2 g Threonine, 2.1 g Serine, 1.8 g Proline and 0.9 g Cysteine.

Example 4

Infant Formula

The formula has the following composition (per 100 g of powder): total fat 27.7 g, total protein 9.5 g, total carbohydrates 57.9 g, Threonine 0.50 g, Cystein 0.22 g, Serine 0.49 g, Proline 0.72 g, Sodium 120 mg, Potassium 460 mg, Chloride 330 mg, Phosphorus 160 mg, Calcium 320 mg, Magnesium 36 mg, Manganese 40 μg, Vitamin A 1800 IU, Vitamin D 310 IU, Vitamin E 6.2 IU, Vitamin C 52 mg, Vitamin K1 42 μg, Vitamin B1 0.36 mg, Vitamin B2 0.78 mg, Vitamin B6 0.39 mg, Niacin 5.2 mg, Folic acid 47 μg, Pantothenic acid 2.3 mg, Vitamin B12 1.6 μg, Biotin 11 μg, Choline 52 mg, Inositol 26 mg, Taurine 42 mg, Carnitine 8.3 mg, Iron 3.1 mg, Iodine 78 μg, Copper 0.31 mg and Zinc 3.9 mg.

The formula is reconstituted by mixing 129 g of powder to 900 mL of water to give 1 L of ready-to-drink preparation. The composition given above can vary to accommodate for local directives concerning the amounts of specific ingredients. Other trace elements (e.g. selenium, chromium, molybdenum, fluoride) may be added in adequate amount according to age.

The invention claimed is:

1. A method for stimulating the immune defenses in a human or animal in need of same, the method comprising:
    orally administering to the human or animal a food product comprising free amino acids, the free amino acids comprising Serine, Proline, Threonine, and a sulfur containing amino acid, wherein Serine, Proline, Threonine, and a sulfur containing amino acid are the only added free amino acids in the food product.

2. The method of claim 1, wherein the human or animal has a chronic disease impacting the gut.

3. The method of claim 1, wherein the food product further comprises an ingredient selected from the group consisting of a source of protein, a source of fat, a source of carbohydrate, a vitamin, a mineral, and combinations thereof.

4. A method for maintaining the integrity of gut barrier in a human or animal in need of same, the method comprising:
    orally administering to the human or animal a food product comprising free amino acids, the free amino acids comprising Serine, Proline, Threonine, and a sulfur containing amino acid, wherein Serine, Proline, Threonine, and a sulfur containing amino acid are the only added free amino acids in the food product.

5. The method of claim 4, wherein the human or animal has a chronic disease impacting the gut.

6. The method of claim 4, wherein the food product is in a form selected from the group consisting of a powder, a liquid concentrate, a ready-to-drink beverage, and combinations thereof.

* * * * *